(12) United States Patent
Kim et al.

(10) Patent No.: US 11,034,786 B2
(45) Date of Patent: Jun. 15, 2021

(54) AMPHIPHILIC TRIBLOCK POLYMER

(71) Applicants: LG CHEM, LTD., Seoul (KR); LG HOUSEHOLD & HEALTH CARE LTD., Seoul (KR)

(72) Inventors: Kyung Oh Kim, Daejeon (KR); Su Jeong Kim, Daejeon (KR); Sun Hwa Lee, Daejeon (KR); Woo Sun Shim, Daejeon (KR); Jeong Ae Yoon, Daejeon (KR); Sung Soo Yoon, Daejeon (KR); Chang Hwan Ju, Daejeon (KR); Jung A Kim, Daejeon (KR); Nae Gyu Kang, Daejeon (KR)

(73) Assignees: LG Chem, Ltd., Seoul (KR); LG Household & Health Care Ltd., Seoul (KR)

( * ) Notice: Subject to any disclaimer, the term of this patent is extended or adjusted under 35 U.S.C. 154(b) by 204 days.

(21) Appl. No.: 16/304,048

(22) PCT Filed: Jun. 16, 2017

(86) PCT No.: PCT/KR2017/006341
§ 371 (c)(1),
(2) Date: Nov. 21, 2018

(87) PCT Pub. No.: WO2017/217817
PCT Pub. Date: Dec. 21, 2017

(65) Prior Publication Data
US 2020/0317845 A1   Oct. 8, 2020

(30) Foreign Application Priority Data

Jun. 16, 2016 (KR) .................. 10-2016-0075039
Jun. 16, 2017 (KR) .................. 10-2017-0076509

(51) Int. Cl.
*C08F 293/00* (2006.01)
*A61K 9/107* (2006.01)
*A61K 47/32* (2006.01)
*C08F 220/06* (2006.01)
*C08F 220/14* (2006.01)

(52) U.S. Cl.
CPC ............ *C08F 293/00* (2013.01); *A61K 9/107* (2013.01); *A61K 47/32* (2013.01); *C08F 220/06* (2013.01); *C08F 220/14* (2013.01); *C08F 2438/01* (2013.01)

(58) Field of Classification Search
CPC ......................... C08F 293/00; C08G 65/00
See application file for complete search history.

(56) References Cited

U.S. PATENT DOCUMENTS

| 6,491,903 | B1 | 12/2002 | Forster et al. | |
|---|---|---|---|---|
| 2003/0170332 | A1* | 9/2003 | Senthilmohan | A61K 36/15 424/770 |
| 2009/0220614 | A1* | 9/2009 | Qin | A61K 9/1273 424/501 |
| 2012/0076978 | A1* | 3/2012 | Millward | B81C 1/00031 428/120 |
| 2015/0033985 | A1* | 2/2015 | Kavanagh | C08K 5/1535 106/170.29 |
| 2016/0271062 | A1 | 9/2016 | Lebouille et al. | |
| 2017/0018801 | A1* | 1/2017 | Grubbs | H01M 10/0525 |
| 2018/0085318 | A1 | 3/2018 | Steendam et al. | |
| 2020/0000936 | A1 | 1/2020 | Dixon et al. | |

FOREIGN PATENT DOCUMENTS

| CN | 101265312 A | 9/2008 |
|---|---|---|
| CN | 102030898 A | 4/2011 |
| EP | 1 225 873 B1 | 3/2006 |
| JP | 2001-508762 A | 7/2001 |
| JP | 5118281 B2 | 1/2013 |
| JP | 2013-522178 A | 6/2013 |
| JP | 2014-521762 A | 8/2014 |
| JP | 2015-071762 A | 4/2015 |
| JP | 2015-154943 A | 8/2015 |
| KR | 10-2014-0147880 A | 12/2014 |
| WO | 2010/068432 A1 | 6/2010 |

* cited by examiner

*Primary Examiner* — Jeffrey C Mullis
(74) *Attorney, Agent, or Firm* — Dentons US LLP

(57) ABSTRACT

The present application relates to an amphiphilic triblock polymer and micelles comprising the amphiphilic triblock polymer. The amphiphilic triblock polymer of the present application can have excellent dispersion properties and excellent water solubility while effectively encapsulating the drug.

14 Claims, 1 Drawing Sheet

[Figure 1]
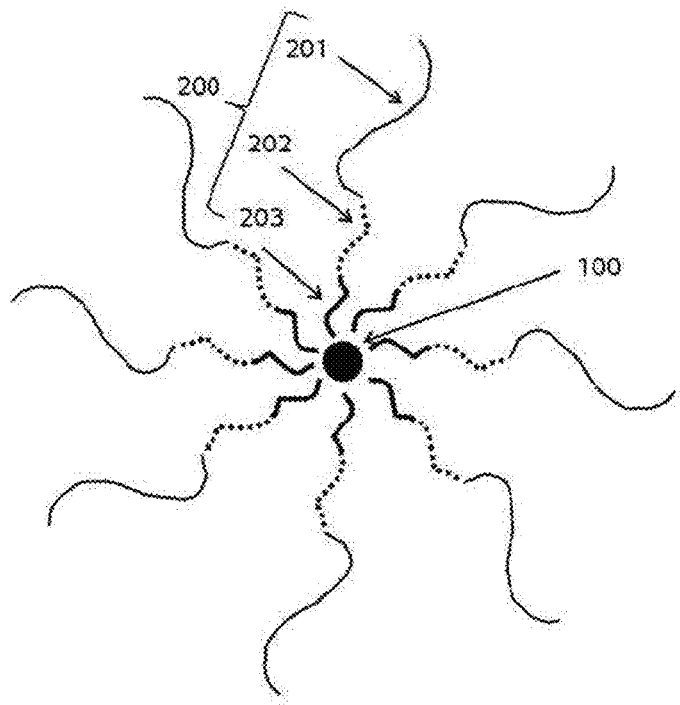
[Figure 2]
|  | Example 1 | Example 2 | Example 3 | Example 4 | Comparative Example 1 | Comparative Example 2 | Comparative Example 3 |
|---|---|---|---|---|---|---|---|
| Aqueous Solution Image | | | | | | | |

AMPHIPHILIC TRIBLOCK POLYMER

TECHNICAL FIELD

The present application relates to an amphiphilic triblock polymer, micelles comprising the same and a method for producing micelles. This application is a National Stage Application of International Application No. PCT/KR2017/006341 filed Jun. 16, 2017, and claims the benefit of priority under Korean Patent Application No. 10-2016-0075039 filed on Jun. 16, 2016 and Korean Patent Application No. 10-2017-0076509 filed on Jun. 16, 2017, the disclosures of which are incorporated herein by reference in their entirety.

BACKGROUND ART

In the field of pharmacy and cosmetics, there has been a demand for the development of dosage forms capable of effectively acting on the skin and improving the condition of the skin while stably collecting various substances having efficacy on the skin in the product.

However, most of drugs were poorly soluble or unstable to bind to or react with other substances, so that they did not exhibit the drugs' efficacy or there were difficulties in formulation.

Accordingly, related studies have been made in order to improve the solubility and the absorption rate in the body of the poorly soluble drug, and for example, methods of modifying the drug structure to increase the solubility or encapsulating it to increase the stability and solubility have been known.

Specifically, surfactants, nano/micro-emulsions, liposomes or amphiphilic triblock polymers have been used for drug encapsulation, and particularly, if the amphiphilic triblock polymer is used, there is an advantage that physicochemical properties are easily controlled.

On the other hand, the polymer used for the encapsulation must be removed after delivering the poorly soluble drug, where high solubility of the polymer in water is required for efficient removal.

DISCLOSURE

Technical Problem

The present application provides an amphiphilic triblock polymer capable of having excellent dispersion characteristics and excellent water solubility while effectively encapsulating a drug.

The present application also provides micelles comprising the amphiphilic triblock polymer and a method for producing the micelles.

The above and other objects of the present application can be all attained by the present application which is described in detail below.

Technical Solution

In one example related to the present application, the present application relates to an amphiphilic triblock polymer. The amphiphilic triblock polymer according to the present application is a triblock copolymer capable of exhibiting phase separation characteristics, which can effectively encapsulate a drug using self-assembly characteristics and can also be included in a pharmaceutical composition or a cosmetic composition, and the like, under a state of having good dispersion properties.

In the present application, the term "amphiphilic triblock polymer" means a polymer simultaneously containing regions having different physical properties, for example, different solubility parameters, which may mean, for example, a polymer containing a hydrophilic region and a hydrophobic region at the same time.

In the present application, the term "hydrophilic or hydrophobic region" means a region contained in a polymer, in such a state that it can be confirmed that each region is phase-separated, for example, while forming a block, where each degree of hydrophilicity or hydrophobicity is relative.

In the present application, the term "self-assembly characteristic" means a phenomenon that the amphiphilic triblock polymer spontaneously undergoes fine phase separation in oil or in water and has constant size regularity.

The amphiphilic triblock polymer according to the present application comprises a first block (A), and a second block (B) and a third block (C) which are phase-separated from the first block (A). Also, the first block (A) has a solubility parameter larger than the solubility parameters of the second block (B) and the third block (C), where the first block has a solubility parameter of 10 $(cal/cm^3)^{1/2}$ or more.

The amphiphilic triblock polymer of the present application may comprise blocks phase-separated from each other to effectively collect a drug, and may exhibit high water solubility over the amphiphilic diblock polymer composed of only the composition of the first block (A) and the second block (B) or the first block (A) and the third block (C).

In the present application, the term "phase-separated from each other" means a state where the hydrophilic block (A) and the hydrophobic block (B, C) do not mix with each other and form the respective blocks in the absence of external action.

The amphiphilic triblock polymer of the present application comprises a first block (A) and a second block (B) and a third block (C) which are phase-separated from the first block (A).

The first block (A) means a hydrophilic region of an amphiphilic triblock polymer, which may comprise, for example, a polymer having a solubility parameter of 10 $(cal/cm^3)^{1/2}$ or more.

The method of obtaining the solubility parameter is not particularly limited and may be followed in a manner known in this field. For example, the parameter may be calculated or obtained according to a method known in the art as a so-called HSP (Hansen solubility parameter).

In another example, the first block (A) may comprise a polymer having a solubility parameter of 13 $(cal/cm^3)^{1/2}$ or more, 14 $(cal/cm^3)^{1/2}$ or more, 15 $(cal/cm^3)^{1/2}$ or more, 16 $(cal/cm^3)^{1/2}$ or more, or 17 $(cal/cm^3)^{1/2}$ or more. The upper limit of the solubility parameter of the first block (A) is not particularly limited, and may be, for example, 25 $(cal/cm^3)^{1/2}$ or less, or 23 $(cal/cm^3)^{1/2}$ or less.

The first block (A) satisfies the solubility parameter as described above and any known polymer can be included as long as it can form a hydrophilic region of an amphiphilic triblock polymer capable of comprising a drug according to the present application.

In one example, the first block (A) may be any one selected from the group consisting of polyethylene glycol, a polyethylene glycol-propylene glycol copolymer, polyvinyl pyrrolidone and polyethyleneimine.

Specifically, the first block (A) may be polyethylene glycol having a number average molecular weight in a range of 500 to 100,000, but is not limited thereto. In the present application, the term "number average molecular weight" may mean an analytical value measured by a magnetic resonance apparatus (NMR), and unless otherwise specified, a molecular weight of any polymer may mean a number average molecular weight of the polymer.

The second block (B) has a solubility parameter of 10 $(cal/cm^3)^{1/2}$ or less, which can be exemplified by a compound represented by Formula 1 below, but is not limited thereto.

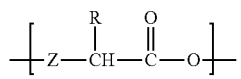

[Formula 1]

In Formula 1, R is hydrogen or an alkyl group, and Z is a group having an alkylene group, an ether group, an ester group or an amide group.

Since the second block (B) of the amphiphilic triblock polymer of the present application has higher water solubility than the third block (C) and is hydrophobic, while using a relatively small amount of the third block (C), the polymer forms micelles and increases the solubility in an aqueous solution, so that the micelles can be more stably present.

The third block (C) may comprise a polymerized unit (C1) of an acrylic monomer or vinyl monomer having a solubility parameter of a single polymer of less than 10.0 $(cal/cm^3)^{1/2}$.

In the present application, the term "acrylic monomer" means (meth)acrylic acid or a derivative thereof. In addition, the term "(meth)acrylic acid" means acrylic acid or methacrylic acid.

The third block (C) of the amphiphilic triblock polymer in the present application is a site for playing a role of forming a micelle shape by encapsulating around the drug adjacent to it. Thus, the third block (C) means a relatively hydrophobic site in the amphiphilic triblock polymer.

In another example, the third block (C) may comprise a polymerized unit (C1) of an acrylic monomer or vinyl monomer having a solubility parameter of a single polymer of less than 9.8 $(cal/cm^3)^{1/2}$ or less than 9.5 $(cal/cm^3)^{1/2}$. The lower limit of the solubility parameter of the acrylic monomer or vinyl monomer is not particularly limited and may be, for example, 2 $(cal/cm^3)^{1/2}$ or more, or 4 $(cal/cm^3)^{1/2}$ or more.

The acrylic monomer can be exemplified by a compound represented by Formula 2 or 3 below, but is not limited thereto.

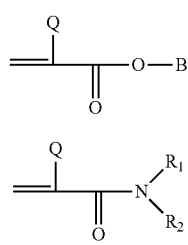

[Formula 2]

[Formula 3]

In Formulas 2 and 3, Q is hydrogen or an alkyl group, and B in Formula 1 is a linear or branched alkyl group, an alicyclic hydrocarbon group, an aromatic substituent group or a carboxyl group, having at least 1 carbon atom and R1 and R2 in Formula 3 are each independently hydrogen, or a linear or branched alkyl group, an alicyclic hydrocarbon group or an aromatic substituent group, having at least 1 carbon atom.

In Formulas 2 and 3, as the alkyl group present in Q, an alkyl group having 1 to 20 carbon atoms, 1 to 16 carbon atoms, 1 to 12 carbon atoms, 1 to 8 carbon atoms or 1 to 4 carbon atoms may be used. The alkyl group may be linear, branched or cyclic. In addition, the alkyl group may be optionally substituted with one or more substituents.

In Formulas 2 and 3, B, R1 and R2 may be each independently a linear or branched alkyl group having at least 1 carbon atom, at least 3 carbon atoms, at least 5 carbon atoms, at least 7 carbon atoms, or at least 9 carbon atoms, which may be optionally substituted or in a un-substituted state. Such a compound comprising a relatively long chain alkyl group is known as a hydrophobic compound. The upper limit of the carbon number in the linear or branched alkyl group is not particularly limited, and for example, may be an alkyl group having at most 20 carbon atoms.

In another example, B, R1 and R2 in Formulas 2 and 3 may be an alicyclic hydrocarbon group, for example, an alicyclic hydrocarbon group having 3 to 20 carbon atoms, 3 to 16 carbon atoms, or 6 to 12 carbon atoms, where an example of such a hydrocarbon group may be exemplified by an alicyclic alkyl group having 3 to 20 carbon atoms, 3 to 16 carbon atoms or 6 to 12 carbon atoms, such as a cyclohexyl group or an isobornyl group. Such a compound having an alicyclic hydrocarbon group is also known as a relatively hydrophobic compound.

In another example, B, R1 and R2 in Formulas 2 and 3 may be an aromatic substituent group, such as an aryl group or an arylalkyl group.

Here, the aryl group may be, for example, an aryl group having 6 to 24 carbon atoms, 6 to 18 carbon atoms, or 6 to 12 carbon atoms. The alkyl group of arylalkyl may be, for example, an alkyl group having 1 to 20 carbon atoms, 1 to 16 carbon atoms, 1 to 12 carbon atoms, 1 to 8 carbon atoms, or 1 to 4 carbon atoms. The aryl group or arylalkyl group may be exemplified by a phenyl group, a phenylethyl group, a phenylpropyl group or a naphthyl group, but is not limited thereto.

In the present application, the substituent which may optionally be substituted in the alkyl group, aryl group or hydrocarbon group, and the like in Formulas 2 and 3 above may be exemplified by halogen such as chlorine or fluorine, an epoxy group such as a glycidyl group, an epoxyalkyl group, a glycidoxyalkyl group or an alicyclic epoxy group, an acryloyl group, a methacryloyl group, an isocyanate group, a thiol group, an alkyl group, an alkenyl group, an alkynyl group or an aryl group, and the like, but is not limited thereto.

The compound represented by Formula 2 above may be, for example, alkyl (meth)acrylate. Here, the term "(meth) acrylate" means acrylate or methacrylate. The alkyl (meth) acrylate may be exemplified by, for example, methyl (meth) acrylate, ethyl (meth)acrylate, n-propyl (meth)acrylate, isopropyl (meth)acrylate, n-butyl (meth)acrylate, t-butyl (meth)acrylate, sec-butyl (meth)acrylate, pentyl (meth)acrylate, hexyl (meth)acrylate, 2-ethylhexyl (meth)acrylate, 2-ethylbutyl (meth)acrylate, n-octyl (meth)acrylate, isobornyl (meth)acrylate, isooctyl (meth)acrylate, isononyl (meth) acrylate or lauryl (meth)acrylate, and the like, but is not limited thereto.

In the present application, among the monomers as above, an appropriate type may be selected and used in consideration of physical properties of the desired amphiphilic polymer.

In one example, in Formula 2, Q may be hydrogen or an alkyl group having 1 to 4 carbon atoms, and B may be an alkyl group having 7 or more carbon atoms or an alicyclic hydrocarbon group having 6 to 12 carbon atoms, without being limited thereto.

The third block (C) may comprise a polymerized unit (C1) of a vinyl monomer having a solubility parameter of a single polymer of less than 10 $(cal/cm^3)^{1/2}$, where the vinyl monomer may be a compound represented by Formula 4 or 5 below.

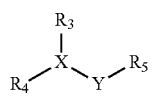

[Formula 4]

In Formula 4, X is a nitrogen atom or an oxygen atom, Y is a carbonyl group or a single bond, R3 and R5 are each independently hydrogen or an alkyl group, or R3 and R5 are linked together to form an alkylene group, and R4 is an alkenyl group (provided that when X is an oxygen atom, R3 is not present).

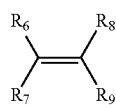

[Formula 5]

In Formula 5, R6, R7 and R8 are each independently hydrogen or an alkyl group, and R9 is a cyano group or an aromatic substituent group.

When Y in Formula 4 is a single bond, a structure in which no separate atom is present in the moiety represented by Y and R5 and X are directly linked can be realized.

In Formula 4, R4 may be, for example, a linear, branched or cyclic alkenyl group having 2 to 20 carbon atoms, 2 to 16 carbon atoms, 2 to 12 carbon atoms, 2 to 8 carbon atoms or 2 to 4 carbon atoms, which may be in an optionally substituted or un-substituted state. Generally, as the alkenyl group, a vinyl group or an allyl group, and the like may be used.

In Formula 4, R3 and R5 may be each independently hydrogen or a linear, branched or cyclic alkyl group having 1 to 20 carbon atoms, 1 to 16 carbon atoms, 1 to 12 carbon atoms, 1 to 8 carbon atoms, or 1 to 4 carbon atoms, or linked together to form an alkylene group having 1 to 20 carbon atoms, 2 to 16 carbon atoms, 2 to 12 carbon atoms, or 2 to 8 carbon atoms. Here, when R3 and R5 form an alkylene group, the compound of Formula 4 may be a cyclic compound.

The vinyl monomer represented by Formula 4 or 5 above may be exemplified by, for example, a styrene-based monomer such as styrene or methyl styrene; acrylonitrile; an amide-based monomer such as an N-vinylamide compound; an ester-based monomer such as a vinyl ester compound; or an ether-based monomer such as a vinyl ether compound, but is not limited thereto and it can be used as a vinyl monomer contained as a polymerized unit in the amphiphilic polymer of the present application without limitation as long as it satisfies the solubility parameter of the single polymer as described above.

Also, the third block (C) may comprise a polymerized unit (C2) of a polymerizable monomer having a functional group capable of forming a hydrogen bond, in addition to the polymerized unit (C1) of the acrylic monomer or vinyl monomer as described above.

As the polymerized unit (C1) of the acrylic monomer or vinyl monomer and the polymerized unit (C2) of the polymerizable monomer having a functional group capable of forming a hydrogen bond, as described above, are simultaneously included in the third block (C), the amphiphilic triblock polymer of the present application can improve collection ability of the target drug and position the drug more stably inside the micelles (core).

Here, the polymerizable monomer having a functional group capable of forming a hydrogen bond is a polymerizable monomer other than the acrylic monomer and the vinyl monomer as described above, which may mean a monomer with a functional group capable of forming a hydrogen bond.

In one example, the functional group of the polymerizable monomer may be exemplified by a hydroxyl group, an amine group, a nitro group, an amino group, an imide group, an alkoxysilane group or a cyano group, and the like, but is not limited thereto, and is not limited as long as it is a functional group which forms interaction with —H in a drug to be described below, specifically, a hydrogen bond, to improve the collection ability of the drug and plays a role of an electron donor capable of positioning the drug more stably inside the micelles (core).

The polymerizable monomer containing an amine group may be exemplified by, for example, 2-aminoethyl (meth) acrylate, 3-aminopropyl (meth)acrylate, N,N-dimethylaminoethyl (meth)acrylate or N,N-dimethylaminopropyl (meth) acrylate, and the like, but is not limited thereto.

The polymerizable monomer containing an alkoxysilane group may be exemplified by, for example, vinyl alkoxysilane, allyl alkoxysilane, (meth)acryloxyalkyl alkoxysilane or vinyl acryloxysilane, and the like. Also, the (meth) acryloxyalkyl alkoxysilane may be exemplified by, for example, 3-(meth)acryloxypropylmethyl dimethoxysilane, 3-(meth)acryloxypropylmethyl diethoxysilane, 3-(meth) acryloxypropyl trimethoxysilane, 3-(meth)acryloxypropyl triethoxysilane, 3-(meth)acryloxymethyl triethoxysilane, or (meth)acryloxymethyl tris(trimethylsiloxy)silane, and the like, but is not limited thereto.

The polymerizable monomer containing a cyano group may be exemplified by, for example, cyanomethyl (meth) acrylate, cyanoethyl (meth)acrylate or cyanopropyl (meth) acrylate, and the like, but is not limited thereto.

Such a polymerizable monomer having a functional group capable of forming a hydrogen bond forms a polymerized unit (C2) in the third block (C), where the polymerized unit (C2) can perform the role of collecting the drug, for example, by being located outside the polymer.

Also, the third block (C) may comprise the polymerized unit (C1) of the acrylic monomer or vinyl monomer and the polymerized unit (C2) of the polymerizable monomer having a functional group capable of forming a hydrogen bond as described above in a predetermined weight ratio.

For example, the weight ratios (C1:C2) of the polymerized unit (C1) of the acrylic monomer or the vinyl monomer having a solubility parameter of a single polymer of less than 10.0 $(cal/cm^3)^{1/2}$ and the polymerized unit (C2) of the polymerizable monomer having a functional group capable of forming a hydrogen bond in the third block (C) may be the same or different. For example, the weight ratio (C1:C2) may be in a range of 1:9 to 9:1. In another example, the weight ratio (C1:C2) may be in the range of 2:8 to 8:2, 3:7 to 7:3 or 4:6 to 6:4. Within the range of such a weight ratio (C1:C2), it is possible to effectively collect the drug and to form the amphiphilic polymer safely dispersed in the aqueous solution.

For example, the third block (C) may have a number average molecular weight in a range of 500 to 100,000. Within such a range, desired hydrophobic properties and collection ability of drugs can be secured.

The amphiphilic triblock polymer of the present application may have the same or different block ratio (A:B+C) of the first block (A), which is a hydrophilic block, and the second and third blocks (B, C), which are hydrophobic blocks.

In addition, the block ratio (B:C) of the second block (B) and the third block (C), which are hydrophobic, may be the same or different.

Specifically, the amphiphilic triblock polymer of the present application can adjust the block ratio (A:B) of the first block (A), which is hydrophilic, and the second block (B), which is hydrophobic, within the range of 1:9 to 9:1, and can adjust the block ratio (B:C) of the second block (B) and the third block (C) within the range of 1:9 to 9:1. Here, the term block ratio means a weight ratio between the respective blocks.

In another example, the block ratio (A:B+C) of the first block (A) and the second and third blocks (B, C) may be 2:8 to 8:2, 3:7 to 7:3 or 4:6 to 6:4.

Within such a range of the block ratio (A:B:C), the desired dispersion characteristics can be effectively secured, and the percutaneous absorption properties of the dosage form can be improved.

The amphiphilic triblock polymer may have a number average molecular weight (Mn) in the range of 1,000 to 500,000.

In another example related to the present application, the present application relates to micelles. The micelles according to the present application may comprise the above-described amphiphilic triblock polymer.

In the present application, the term "micelle" may mean a particle of a size from several nanometers to tens of thousands nanometers having a core/shell structure by self-assembly characteristics of an amphiphilic triblock polymer.

The micelles comprising the amphiphilic triblock polymer of the present application can have excellent encapsulation properties and excellent dispersion characteristics in oil or in water and can also have excellent stability, thereby being effectively applied to dosage forms having excellent percutaneous absorption properties.

Such micelles may further comprise, for example, a drug encapsulated by an amphiphilic triblock polymer.

In one example, as shown in FIG. 1, the micelle of the present application may be a structure comprising a drug (100) and an amphiphilic triblock polymer (200) encapsulating the drug (100). The amphiphilic triblock polymer (200) may comprise a first block (201) and a second block (202) and a third block (203), where the third block (203) of the amphiphilic triblock polymer (200) may have a structure adjacent to the drug (100). Here, the encapsulation is a term meaning a structure in which an amphiphilic triblock polymer surrounds a drug, as in FIG. 1, which is used in the present application in the same meaning as "collection."

Typically, the drug is poorly soluble, but the drug of the present application is encapsulated by an amphiphilic triblock polymer having both a hydrophobic region and a hydrophilic region, thereby ensuring excellent dispersion characteristics of the drug in oil or in water.

Also, in the case of the micelles of the present application, they may be effectively dispersed in oil or in water in a state where the stability is secured, by comprising an amphiphilic triblock polymer having an excellent interaction with a specific drug.

The drug contained in the micelles of the present application is not particularly limited, but may include, for example, a physiologically active substance.

In one example, the bioactive material may be poorly soluble.

Such a physiologically active substance may be, for example, any one selected from the group consisting of genistein, daidzein, prangenidin or a derivative thereof; polyphenols; or a mixture thereof.

The genistein, daidzein, prangenidin or a derivative thereof as one example of the physiologically active substance means a phenolic compound or its glycoside contained in soybean, which has a similar structure to estrogen of a female hormone, and has an excellent antioxidant effect or the like and thus is used in various fields from skin care to anticancer therapy.

Isoflavone such as genistein, daidzein, prangenidin or a derivative thereof is a phenolic compound, which comprises intra-molecular hydrogen (—H), where the intra-molecular hydrogen is subjected to a hydrogen bond with the functional group that the hydrogen bond is possible, which is included in the third block (C) of the amphiphilic triblock polymer, whereby the stability of the drug positioned inside the micelles can be improved.

Specifically, the isoflavone may be genistein or a glycoside of the genistein, for example, acetyl genistein or malonyl genistein, and the like, but is not limited thereto.

The drug contained in the micelles may be included in the micelles in such an amount to be capable of expressing the physiological activity when the micelles have been prepared into a dosage form.

In one example, the drug content may be in a range of 1 to 60 wt %, 1 to 50 wt %, 1 to 40 wt %, or 1 to 20 wt %, relative to the total weight of the micelles. If the drug content is more than 60 wt %, effective collection may not be achieved, and the drug may flow out of the micelles to be aggregated into a crystalline form or modified.

In one example, the micelles may have an average particle size in a range of 1 nm to 10,000 nm. The average particle size of the micelles is a value measured by a dynamic light scattering method which may be a range covering a particle diameter of a single micelle or micelle aggregates themselves.

As described above, the micelles according to the present invention may have a different block ratio (A:B+C) of the first block (A), the second block (B) and the third block (C) and may also have good encapsulation properties, dispersion properties in an aqueous solution and dosage forms, by comprising the amphiphilic triblock polymer containing a functional group capable of performing a predetermined interaction with the drug.

In another embodiment related to the present application, the present application relates to a composition comprising micelles. The composition according to the present application may be a composition for producing particles comprising micelles containing the amphiphilic triblock polymer, where the composition for producing particles may be a pharmaceutical or cosmetic composition.

The composition for producing particles of the present application comprises micelles formed due to self-assembly characteristics of an amphiphilic triblock polymer. In addition, the amphiphilic triblock polymer forming such micelles may be encapsulating, for example, a drug.

More specifically, the micelles contained in the composition for producing particles may comprise an amphiphilic triblock polymer and a drug encapsulated by the amphiphilic triblock polymer.

In one example, when the composition is a pharmaceutical composition, the drug in the micelle may be included in the composition in a pharmaceutically acceptable form. In addition, the pharmaceutical composition may further comprise a pharmaceutically acceptable carrier.

In one example, the pharmaceutical composition or cosmetic composition may be in a form of a water-in-oil or water-in-oil emulsion.

Micelles in the composition may, for example, form aggregates. Such micelle aggregates may be formed due to van der Waals force between hydrophobic regions. The size of such micelle aggregates may be, for example, in a range of 10 nm to 10,000 nm.

In another example according to the present application, the present application relates to a method for producing micelles according to the present application. The production method according to the present application may comprise steps of producing an amphiphilic triblock polymer according to the present application and mixing the amphiphilic triblock polymer and a drug.

In one example, the step of producing an amphiphilic triblock polymer may be a step of producing an amphiphilic triblock polymer in which in an amphiphilic A-B-C triblock polymer separated into a first block (A), and a second block (B) and a third block (C), phase-separated from the first block (A), the solubility parameter of the first block (A) is greater than the solubility parameters of the second block (B) and the third block (C) and the solubility parameter of the first block is 10 $(cal/cm^3)^{1/2}$ or more of the amphiphilic triblock polymer.

Specifically, in the step of producing the amphiphilic triblock polymer, the method of polymerizing the polymer forming the first and second blocks (A, B) and a monomer forming the third block (C) is not particularly limited, but for effectively attaining a narrow molecular weight distribution and the desired molecular weight, living radical polymerization, for example, atom transfer radical polymerization (ATRP) can be used.

More specifically, the amphiphilic triblock polymer of the present application may be produced by reacting the polymer forming the first and second blocks (A, B) containing halogen atoms with a transition metal complex catalyst to produce radicals, where such radicals accept double bond site electrons of an acrylic monomer or vinyl monomer for forming the third block, and forming the third block (C1) having the polymerized unit (C1) of the acrylic monomer or vinyl monomer, but is not limited thereto.

The polymer forming the first and second blocks (A, B) is, for example, a polymer comprising halogen atoms, where if the polymer for forming the first and second blocks (A, B) without any halogen atom is used, the method may further comprise a step of preparing an initiator for ATRP through the reaction with a compound comprising a halogen atom.

The step of mixing the drug with the amphiphilic triblock polymer thus produced may comprise, for example, dissolving the amphiphilic triblock polymer in a predetermined organic solvent, for example, ethanol or the like, and then mixing the prepared solution and a solution comprising a drug.

Furthermore, the method may comprise a process of removing the solvent as a subsequent process after the process, but is not limited thereto, and known additional processes may be involved between the respective processes or as subsequent processes.

The temperature in the process of removing the solvent differs depending on the boiling point of each solvent, and for example, the solvent may be removed at a temperature of 50° C. or higher, without being limited thereto.

Advantageous Effects

The present application can provide an amphiphilic triblock polymer capable of effectively encapsulating a drug and having good dispersion properties in aqueous solution.

The present application can also provide micelles which have high stability to drugs and good water solubility and which can be removed only with water without using an additional detergent, and a method for producing the micelles.

BRIEF DESCRIPTION OF DRAWINGS

FIG. 1 is a schematic diagram of a micelle comprising an amphiphilic triblock polymer according to the present application.

FIG. 2 is images confirming the turbidity of amphiphilic triblock polymers or amphiphilic polymers according to examples and comparative examples in the aqueous solution state depending on the water solubility.

MODE FOR INVENTION

Hereinafter, the present application will be described in more detail by way of examples, but the examples are merely examples limited to the gist of the present application. Furthermore, it is obvious to those skilled in the art that the present application is not limited to the process conditions set forth in the following examples and they may be optionally selected within the scope of the conditions necessary for achieving the object of the present application.

Example 1

Production of Amphiphilic Triblock Polymer (P1)

After removing moisture from polyethyleneglycol monomethyl ether (mPEG-OH) forming the first block (A), 20 equivalents of ε-caprolactone and 0.05 equivalents of tin (II) ethylhexanoate, relative to the —OH functional group, are added thereto, and reacted at 140° C. for 4 hours under nitrogen atmosphere. The reaction solution was cooled to room temperature, dissolved in dichloromethane (DCM) at a concentration of 30%, precipitated in diethyl ether to remove impurities and dried to obtain a white powdery form of PEG-PCL (polyethylene glycol monomethyl ether-poly (ε-caprolactone)) polymer (A-B).

3 equivalents of triethylamine (TEA) and 2 equivalents of 2-bromoisobutyryl bromide, relative to the —OH functional group of the prepared block polymer, are added thereto and reacted to produce an initiator for ATRP. Then, a bromine-terminal PEG-PCL polymer from which impurities are removed by repeating a process of precipitation in a solvent of diethyl ether twice and drying, is dissolved in a reaction solvent (ethanol) and methyl methacrylate (MMA) is introduced in a molar ratio to be produced. After the flask was sealed with a rubber stopper, the dissolved oxygen was removed by nitrogen purging and stirring for 30 minutes at room temperature, and then the flask was immersed in an oil bath set at 60° C., the catalyst solution and the catalyst reducing agent were introduced thereto, and the reaction was carried out for 24 hours to produce an amphiphilic triblock polymer (A-B-C). The catalyst was used by dissolving CuBr$_2$ 100 ppm (mole)/TPMA 2 equivalents (vs. Cu) in ACN, and as the catalyst reducing agent, 6 equivalents (vs. Cu) of V-65 was used.

Example 2

Production of Amphiphilic Triblock Polymer (P2)

An amphiphilic triblock polymer (A-B-C) was produced by carrying out the same manner as in Example 1, except that the bromine-terminal PEG-PCL polymer produced in the same manner as in Example 1 was dissolved in a reaction solvent (ethanol) and MMA and N,N-dimethylaminoethyl methacrylate (DMAEMA) were introduced in a molar ratio to be produced.

Example 3

Production of Amphiphilic Triblock Polymer (P3)

An amphiphilic triblock polymer (A-B-C) was produced by carrying out the same manner as in Example 1, except that the bromine-terminal PEG-PCL polymer produced in the same manner as in Example 1 was dissolved in a reaction solvent (ethanol) and MMA and hydroxyl ethyl methacrylate (HEMA) were introduced in a molar ratio to be produced.

Example 4

Production of Amphiphilic Triblock Polymer (P4)

An amphiphilic triblock polymer (A-B-C) was produced by carrying out the same manner as in Example 1, except that the bromine-terminal PEG-PCL polymer produced in the same manner as in Example 1 was dissolved in a reaction solvent (ethanol) and MMA and 3-methacryloxypropyl methyl dimethoxy silane were introduced in a molar ratio to be produced.

Comparative Example 1

Production of Amphiphilic Triblock Polymer (P5)

The bromine-terminal PEG-PCL polymer produced in the same manner as in Example 1 is dissolved in a reaction solvent (ethanol) and MMA and DMAEMA (N,N-dimethylaminoethyl methacrylate) are introduced in a molar ratio to be produced. After sealing the flask with a rubber stopper, the dissolved oxygen was removed by nitrogen purging and stirring at room temperature for 30 minutes, and then the flask was immersed in an oil bath set at 60° C., and the catalyst solution and the catalyst reducing agent were introduced and the reaction was carried out for 24 hours to produce an amphiphilic triblock polymer (A-B-C). The catalyst was used by dissolving CuBr$_2$ 100 ppm (mole)/TPMA 2 equivalents (vs. Cu) in ACN, and as the catalyst reducing agent, 6 equivalents (vs. Cu) of V-65 was used.

Comparative Example 2

Production of Amphiphilic Polymer (P6)

mPEG-OH forming the first block (A), 3 equivalents of TEA and 2 equivalents of 2-bromoisobutyryl bromide, relative to the —OH functional group, are added thereto, and reacted to produce an initiator for ATRP. Impurities are removed by repeating a process of precipitating in a solvent of diethyl ether twice and drying. The prepared bromine-terminal PEG polymer is dissolved in a reaction solvent (ethanol) and MMA and DMAEMA are introduced in a molar ratio to be produced. After the flask was sealed with a rubber stopper, the dissolved oxygen was removed by nitrogen purging and stirring for 30 minutes at room temperature, and then the flask was immersed in an oil bath set at 60° C., the catalyst solution and the catalyst reducing agent were introduced thereto, and the reaction was carried out for 24 hours to produce an amphiphilic polymer (A-C). The catalyst was used by dissolving CuBr$_2$ 100 ppm (mole)/TPMA 2 equivalents (vs. Cu) in ACN, and as the catalyst reducing agent, 6 equivalents (vs. Cu) of V-65 was used.

Comparative Example 3

Production of Amphiphilic Polymer (P7)

After removing moisture from mPEG-OH forming the first block (A), 20 equivalents of ε-caprolactone and 0.05 equivalents of tin (II) ethylhexanoate, relative to the —OH functional group, are added thereto and reacted at 140° C. for 4 hours under nitrogen atmosphere. The reaction solution is cooled to room temperature, dissolved in DCM (dichloromethane) at a concentration of 30%, precipitated in diethyl ether to remove impurities and dried to obtain a white powdery PEG-PCL amphiphilic polymer (A-B).

Experimental Example 1—Evaluation of Block Ratio and Molecular Weight of the Produced Amphiphilic Polymer The block ratio and molecular weight of the produced amphiphilic triblock polymers (P1-P5) and amphiphilic polymer (P6-P7) were evaluated by the following methods and shown in Table 1.

Specifically, the polymer solution was solidified through a purification step of the polymer solution in which the catalyst was completely removed and then the block ratio of the amphiphilic polymer was confirmed through $^1$H NMR analysis. In the purification of the polymer solution, the polymer solution is solidified by passing it through an alumina column to remove the copper complex catalyst and then dropping it to the excess amount of diethyl ether under stirring to remove the residual monomers. The solidified polymer is dried in a vacuum oven for 24 hours. The amphiphilic polymer purified by the above method is dissolved in a solvent of CDCl$_3$ and measured with a $^1$H NMR analysis instrument.

As an analytical result of Examples 1 to 4, no 1H peak derived from CH$_2$=C(CH$_3$)— of the double bond terminal was confirmed, and accordingly, it can be confirmed that no unreacted monomer is present.

Also, in the case of Examples 1 to 4 and Comparative Examples 1 to 3, since 3H peaks derived from —OCH$_3$ of the ethylene glycol block terminal were confirmed at around 3.2 ppm, and the ratio and molecular weight of each polymer block were calculated, based on the above. Since peaks of about 450 H (4H X repeating units: 113) derived from —CH$_2$CH$_2$O— of ethylene glycol formed into the polymer appeared in the region of 3.6-3.8 ppm, and in the case of Examples 1 to 4 and Comparative Examples 1 and 2, 3H peaks derived from —CH$_3$ adjacent to the main chain of methyl methacrylate formed into the polymer appeared in the region of 3.5-3.6 ppm, the content of each constituent monomer was calculated as a mass fraction through an area ratio thereof.

In the case of Examples 2 to 4 and Comparative Examples 1 and 2, since 2H peaks derived from —OCH$_2$— adjacent to —COO— of dimethylaminoethyl methacrylate, hydroxyethyl methacrylate, and 3-methacryloxypropylmethyl dimethoxysilane side chains formed into the polymer appeared in the region of 4.0-4.2 ppm, the content of each constituent monomer was calculated as a mass fraction through an area ratio thereof. In the case of Comparative Examples 1 and 3, since 2H peaks derived from the first —$CH_2$— on the right of —CO— in —($COCH_2CH_2CH_2CH_2CH_2$—O)n-, which is a chain of caprolactone formed into the polymer, appeared in the region of 2.3-2.4 ppm, the molecular weight was confirmed through the 3H peak area derived from —$OCH_3$ of the ethylene glycol terminal and the 2H peak area derived from the first —$CH_2$— on the right of —CO— of caprolactone.

TABLE 1

|  | Molecular Weight (Mn, A:B:C) | Block Ratio (A:B:C) | Weight Ratio of Third Polymerized Units (C1:C2) |
|---|---|---|---|
| Example 1 | 12,000 (5000:2000:5000) | 41.5:16.5:42 | 100:0 |
| Example 2 | 12,000 (5000:2000:5000) | 41.5:16.5:42 | 80:20 |
| Example 3 | 12,000 (5000:2000:5000) | 41.5:16.5:42 | 80:20 |
| Example 4 | 12,000 (5000:2000:5000) | 41.5:16.5:42 | 80:20 |
| Comparative Example 1 | 12,000 (5000:2000:5000) | 41.5:16.5:42 | 50:50 |
| Comparative Example 2 | 12,000 (5000:0:7000) | 41.6:0:58.4 | 80:20 |
| Comparative Example 3 | 9,900 (5000:4900:0) | 50.5:49.5:0 | — |

C2 of Example 2, Comparative Example 1 and Comparative Example 2: DMAEMA
C2 of Example 3: HEMA
C2 of Example 4: 3-methacryloxypropyl methyldimethoxysilane Experimental Example 2—Confirmation of Turbidity of Micelles For confirming water solubility of the produced amphiphilic triblock polymers (P1-P5) and amphiphilic polymers (P6-P7), the turbidity was evaluated by the following method and shown in Table 2.

Specifically, a solution in which 1 g of the polymer was dissolved in 100 mL of distilled water was prepared. The solution was stirred at 50° C. for about 1 hour and then stabilized at room temperature for 3 hours. The light transmittance of this solution at 600 nm was measured using a UV/VIS spectrometer from Agilent, and then the turbidity (ABS) was calculated from Equation 1 below.

$$\text{Turbidity(Absorbance, ABS)} = \text{Log}\left(\frac{1}{\text{Transmittance}(T)}\right) \quad [\text{Equation 1}]$$

TABLE 2

|  | Example | | | | Comparative Example | | |
|---|---|---|---|---|---|---|---|
|  | 1 | 2 | 3 | 4 | 1 | 2 | 3 |
| Turbidity (ABS) | 0.12 | 0.02 | 0.02 | 0.02 | 0.33 | 2.25 | 0.46 |

Experimental Example 3—Preparation of Micelle and Confirmation of Drug Dissolution Concentration Using the synthesized amphiphilic triblock polymers (P1-P5) and amphiphilic polymers (P6-P7), umbelliferone, as a poorly soluble material and a similar structure of the above-mentioned drugs, was encapsulated. First, a solution, in which 3 g of the polymer and 3 g of umbelliferone were dissolved in 100 mL of ethanol, was prepared. The solution was slowly added to 300 mL of distilled water under stirring, and then left to stand for a certain period of time for evaporation of the ethanol solvent. The prepared solution was diluted with 10 times of distilled water and stored at room temperature (25° C.) for 7 days to allow precipitation of non-encapsulated umbelliferone. The precipitated umbelliferone was removed by filtration with a syringe filter (pore size: 0.45 μm) and then the content of umbelliferone was measured using a UV/VIS spectrometer. The drug loading capacity and drug loading efficiency were calculated by the following equations and the particle size of the micelles comprising the drug-collecting amphiphilic triblock polymer or amphiphilic polymer was measured using Zetasizer 3000 from Malvern.

$$\text{Loadin capacity (\%)} = \frac{\text{Dye capacity}}{\text{Polymer capacity} + \text{Dye capacity}} \times 100 \quad [\text{Equation 2}]$$

$$\text{Loading efficieny (\%)} = \frac{\text{Residual dye concentration after wash}}{\text{Initial input dye concentration}} \times 100 \quad [\text{Equation 3}]$$

The results of measuring the size of micelle particles and the resulting drug loading capacity and drug loading efficiency were shown in Table 3 below.

TABLE 3

|  | Example | | | | Comparative Example | | |
|---|---|---|---|---|---|---|---|
|  | 1 | 2 | 3 | 4 | 1 | 2 | 3 |
| Particle size (diameter, nm) | 131 | 125 | 121 | 124 | 230 | 125 | 100 |
| Loading capacity (%) | 6 | 16 | 15 | 11 | 5 | 10.7 | 1 |
| Loading efficiency (%) | 32 | 80 | 75 | 68 | 43 | 60 | 6 |

EXPLANATION OF REFERENCE NUMERALS

100: drug
200: amphiphilic triblock polymer
201: first block (A)
202: second block (B)
203: third block (C)

The invention claimed is:
1. An amphiphilic triblock (A-B-C) polymer having:
a first block (A); and
a second block (B) and a third block (C) which are phase-separated from said first block (A),
wherein said first block (A) has a solubility parameter larger than the solubility parameters of the second block (B) and the third block (C), where the first block has a solubility parameter of 10 $(\text{cal/cm}^3)^{1/2}$ or more,
wherein the second block (B) has higher water solubility than the third block (C) and is hydrophobic,
wherein the third block (C) comprises a polymerized unit C1 of an acrylic monomer or vinyl monomer, and a polymerized unit C2 of a polymerizable monomer having a functional group capable of forming a hydrogen bond, and the weight ratio C1:C2 is in a range of 6:4 to 9:1.

2. The amphiphilic triblock polymer according to claim 1, wherein the first block (A) is any one selected from the group consisting of polyethylene glycol, a polyethylene glycol-propylene glycol copolymer, polyvinyl pyrrolidone and polyethyleneimine.

3. The amphiphilic triblock polymer according to claim 1, wherein the second block (B) is a compound represented by Formula 1 below:

[Formula 1]

wherein, R is hydrogen or an alkyl group, and Z is a group having an alkylene group, an ether group, an ester group or an amide group.

4. The amphiphilic triblock polymer according to claim 1, wherein said acrylic monomer is a compound represented by Formula 2 or Formula 3 below:

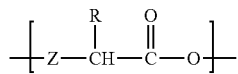

[Formula 2]

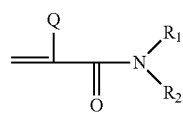

[Formula 3]

wherein, Q is hydrogen or an alkyl group, and B in Formula 2 is a linear or branched alkyl group, an alicyclic hydrocarbon group, an aromatic substituent group or a carboxyl group, having at least 1 carbon atom and $R_1$ and $R_2$ in Formula 3 are each independently hydrogen, or a linear or branched alkyl group, an alicyclic hydrocarbon group or an aromatic substituent group, having at least 1 carbon atom.

5. The amphiphilic triblock polymer according to claim 4, wherein Q in Formula 2 above is hydrogen or an alkyl group having 1 to 4 carbon atoms, and B is an alkyl group having at least 1 carbon atom or an alicyclic hydrocarbon group having 6 to 12 carbon atoms.

6. The amphiphilic triblock polymer according to claim 1, wherein the vinyl monomer is a compound represented by Formula 4 or Formula 5 below:

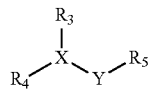

[Formula 4]

wherein, X is a nitrogen atom or an oxygen atom, Y is a carbonyl group or a single bond, $R_3$ and $R_5$ are each independently hydrogen or an alkyl group, or $R_3$ and $R_5$ are linked together to form an alkylene group, and $R_4$ is an alkenyl group (provided that when X is an oxygen atom, $R_3$ is not present);

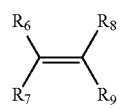

[Formula 5]

wherein, $R_6$, $R_7$ and $R_8$ are each independently hydrogen or an alkyl group, and $R_9$ is a cyano group or an aromatic substituent group.

7. The amphiphilic triblock polymer according to claim 1, wherein said functional group capable of forming a hydrogen bond is a hydroxyl group, an amine group, a nitro group, an amino group, an imide group, an alkoxysilane group or a cyano group.

8. The amphiphilic triblock polymer according to claim 1, wherein the ratio (A:B+C) of the first block (A) and the sum of the second block (B) and the third block (C) is 1:9 to 9:1.

9. The amphiphilic triblock polymer according to claim 1, wherein the ratio (B:C) of the second block (B) and the third block (C) is 1:9 to 9:1.

10. Micelles comprising the amphiphilic triblock polymer according to claim 1.

11. The micelles according to claim 10, further comprising a drug encapsulated by the amphiphilic triblock polymer.

12. The micelles according to claim 11, wherein said drug is any one selected from the group consisting of genistein, daidzein, prangenidin or a derivative thereof; polyphenols; and a mixture thereof.

13. The micelle according to claim 10, having an average particle diameter in a range of 1 to 10,000 nm.

14. A composition for producing particles, comprising the micelles according to claim 10.

* * * * *